United States Patent [19]
Galitzer

[11] Patent Number: 5,792,142
[45] Date of Patent: Aug. 11, 1998

[54] CUTTING TIP

[75] Inventor: Barry D. Galitzer, Fanwood, N.J.

[73] Assignee: Howmedica, Inc., New York, N.Y.

[21] Appl. No.: 603,952

[22] Filed: Feb. 16, 1996

[51] Int. Cl.[6] .......................... A61B 17/58; A61B 17/84
[52] U.S. Cl. .................. 606/65; 606/72; 606/73; 606/80; 606/232; 411/386; 411/387; 411/402
[58] Field of Search .................. 606/65, 72, 73, 606/79, 80, 167, 170, 180, 232; 411/386, 387, 402

[56] References Cited

U.S. PATENT DOCUMENTS

| | | |
|---|---|---|
| 4,632,100 | 12/1986 | Somers et al. |
| 4,978,350 | 12/1990 | Wagenknecht |
| 5,370,662 | 12/1994 | Stone et al. .......................... 606/232 |

OTHER PUBLICATIONS

Soft Tissue Attachment in 30 Seconds (Zimmer Brochure—Oct. 1989).

Fracture Management—Mini-Statak Soft Tissue Attachment Device (Zimmer Brochure—Feb. 1992).

*Primary Examiner*—Michael Buiz
*Assistant Examiner*—Daphja Shai
*Attorney, Agent, or Firm*—Peter C. Richardson; Lawrence C. Akers; Elizabeth O. Slade

[57] ABSTRACT

A new cutting tip and a very simple method for making the tip are given. The tip has no flutes but has a built-in chip clearance. It is self-drilling, self-tapping, and self-locating and can be positioned on a threaded or unthreaded member. When it is the tip on a suture anchor, it maximizes holding strength of the anchor.

15 Claims, 6 Drawing Sheets

CUTTING TIP

BACKGROUND OF THE INVENTION

This invention relates generally to a cutting tip for use on any threaded member (or unthreaded member) and to a method of producing such a cutting tip. The invention relates in particular to a cutting tip which is especially useful on an orthopedic suture anchor (where having a large number of threadings over a short distance is desired).

In the prior art, a large variety of designs for cutting tips exist.

In the field of orthopedics, it is very important to be able to drill holes into bones and tissue. An example of a design for use in advantageously drilling holes into bones is a pin marketed by Howmedica and referred to as the Apex® pin. In U.S. Pat. No. 4,978,350, which is hereby incorporated herein by reference, transcutaneous pins which can pass through flesh and bone and which afford a drilling (i.e., a tapping) of very high quality are described and claimed.

Despite the existence of these and many other types of devices having a variety of cutting tips, yet another cutting tip on a suture anchor was sought which would have particular advantages. These advantages include being easily manufactured, self-tapping (i.e., having its own threading), self-drilling (i.e., does not require that another device be first inserted so as to produce a hole), self-locating (i.e., will maintain its position upon insertion), especially suitable for use as a cutting tip on a suture anchor or soft tissue anchor with a large number of threadings located over a short distance and with the number of full threads being maximized, as well as many other advantages as compared with the cutting tips already known in the prior art.

An object of this invention is a self-penetrating and self-locating tip suitable for use as the tip on any threaded member, including for example on a suture anchor, a tap, a drill, a reamer, a screw, and a pin, with the tip having built-in chip clearance.

Another object is a cutting tip suitable for use on a pin having no threads.

Yet another object of this invention is a cutting tip having many advantages and being very easily made.

A further object of this invention is a method of making a self-penetrating and self-locating tip which is very easily made in a simple operation and which is especially useful as the tip on a suture anchor so as to produce a self-drilling and self-tapping suture anchor with a self-locating and self-penetrating tip.

A still further object of this invention is a cutting tip produced by a new method of making a self-penetrating and self-locating tip in a very easy operation.

SUMMARY OF THE INVENTION

According to the invention, a new cutting tip which is self-penetrating and self-locating comprises a non-fluted cutting tip having concave curved facets and a full, complete and uninterrupted first thread (located adjacent to the cutting tip) and being suitable for use as the tip on any threaded member.

Further, according to the invention, the new cutting tip of the invention is the cutting tip on a suture anchor, on a tap, on a screw, and on a pin (either with or without threads).

Also, according to the invention, the cutting tip of the invention has no flutes (which would result in interrupted partial threads when the tip is located on a threaded member), but instead has a plurality of curved (as opposed to flat) facets which are concave in shape; and it can be the cutting tip on any threaded member or on an unthreaded pin.

Also, according to the invention a method of forming the cutting tip of the invention on a threaded member having a pitch p comprises:

(a) holding a threaded member having a center axis in a stationary first position;

(b) locating from the end of the threaded member, in a first plunge cut, moving an end mill cutting tool (having a radius r) with respect to and toward the center axis of the threaded member so that the final offset distance of the end mill with respect to the threaded member is approximately equal to the radius r of the end mill, thus forming a first curved facet in the cutting tip;

(c) turning the threaded member through a first angle α with respect to the stationary first position, fixing the threaded member, and then making a second plunge cut as in step (b) above;

(d) turning the threaded member through a second angle α with respect to the stationary first position, fixing the threaded member, and then making a third plunge cut.

In a preferred embodiment of the method of the invention, the angle α is approximately 120° and three curved facets are produced on the cutting tip.

If the angle α is approximately 90° and a fourth plunge cut is made as described above, four curved facets result on the cutting tip; and if the angle α is approximately 75° and five plunge cuts are made, five curved facets result on the cutting tip.

Further, according to the invention, a new cutting tip is formed by the method of the invention.

BRIEF DESCRIPTION OF THE DRAWINGS

FIG. 11 (photograph 1) corresponds substantially to FIGS. 1 and 2 but with the tip end pointing to the left rather than to the right.

FIG. 12 (photograph 2) corresponds substantially to FIG. 3 but with the tip end pointing to the left instead of to the right.

FIG. 13 (photograph 3) corresponds substantially to FIG. 4.

FIG. 14 (photograph 4) also corresponds substantially to FIG. 4 but with the tip rotated clockwise approximately 270°.

FIG. 15 (photograph 5) shows the cutting tip and the beginning of the first full, complete and uninterrupted thread located adjacent to the cutting tip with the different radii clearly apparent.

DETAILED DESCRIPTION OF THE PREFERRED EMBODIMENTS

Figure 1:
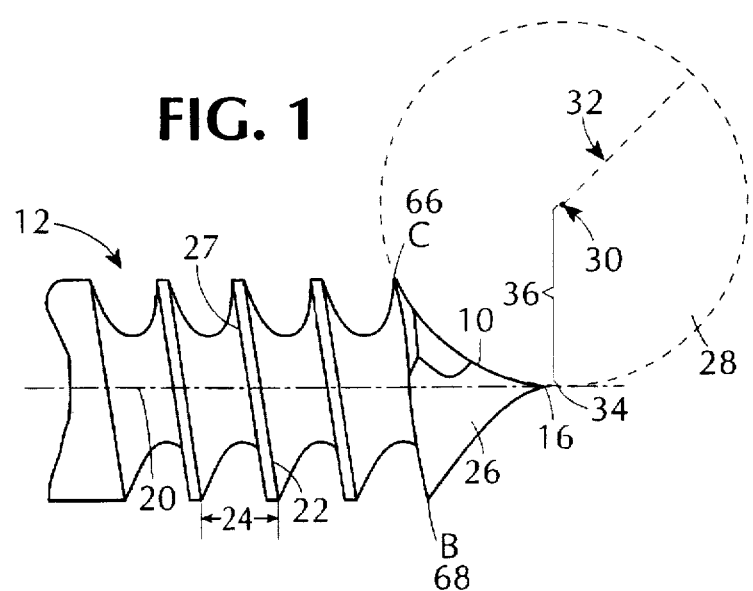
FIG. 1 is a lateral plan view of a preferred embodiment of a cutting tip of the invention which was actually manufactured, positioned on a threaded member, this embodiment having in particular three concave curved facets. Also shown are phantom lines (indicating a cross-section of a cutter which is also referred to as an end mill cutting tool and which is used to form the cutting tip).

Referring to the drawing, in FIG. 1 an embodiment of a cutting tip 10 of the invention having three facets is shown in a plan view, as viewed laterally toward a facet 26. The cutting tip 10 is preferably positioned on a threaded member 12 (as opposed to on an unthreaded member).

Figure 2:
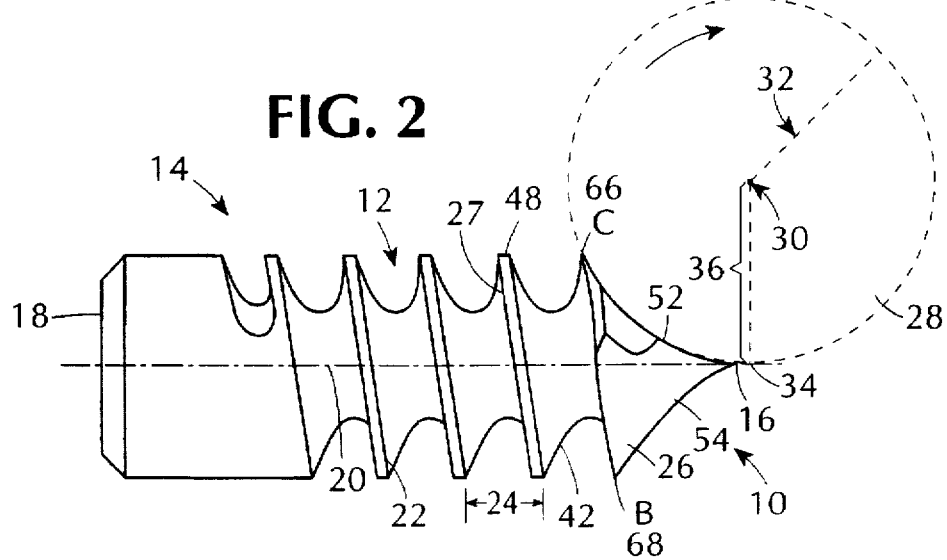
FIG. 2 is a lateral plan view of the cutting tip of FIG. 1 in which the threaded member is (in a particular, preferred embodiment) a suture anchor.

In FIG. 2, the threaded member 12 of FIG. 1 is (in a particular preferred embodiment) a suture anchor 14 having a tip end 16 (as in FIG. 1) and a second end 18, to which a suture (not shown) will be attached in any suitable manner.

Figure 10:
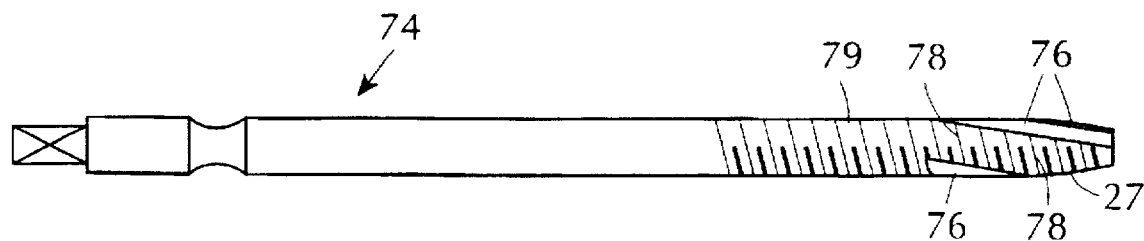
FIG. 10 is a lateral plan view of an embodiment of an Apex® pin (which is FIG. 1 in U.S. Pat. No. 4,978,350), showing flutes which have been used in the prior art and which are in contradistinction to the non-fluted cutting tip of the present invention.

The threaded member 12 of FIGS. 1 and 2 has a center axis 20, a number of threads 22 (which can be chosen as desired), and a tip end 16. Between two adjacent threads 22, pitch 24 is present. Cutting tip 10 of the invention has a plurality of concave curved facets. In a preferred embodiment, there are three such facets, one facet 26 of which is shown in FIG. 1 and in FIG. 2. No flute or flutes (which are similar to troughs and examples of which are shown in FIG. 10) are present in the cutting tip 10 of the invention. It is noted that a result of a flute is a plurality of interrupted threads, including an interrupted thread 27 located adjacent to the tip end. See FIG. 10 below. However, in the cutting tip 10 of the invention, when the tip 10 is positioned on a threaded member 12, the facets are cut into (and from) thread (a portion 40 of which remains and is visible); and the thread 27 located adjacent to tip 10 is full and complete and uninterrupted.

One or more threads can be used to make the cutting tip of the invention. The greatest number of threads that will be removed will have a length equal to the radius of the cutter.

Also represented in FIGS. 1 and 2 (in phantom lines) is a cross-section of an end mill cutting tool 28 (also referred to as a cutter) which is used in the preferred method of the invention to form the cutting tip 10 of the invention. Cutter 28 has a cutter center 30, a cutter radius 32, and a point of tangency 34 to the center axis 20 of the threaded member 12. The offset distance 36 between the cutter center 30 and the center axis 20 of the threaded member 12 is indicated and is approximately equal to (or a little less than) the end mill radius 32. This will be further described below with respect to the preferred method of forming the cutting tip. Also, size and positioning of the cutter can be varied, provided that the multi-faceted tip of the invention results.

The presently preferred method of forming the cutting top 10 of the invention on a threaded member 12 comprises:

(a) holding a threaded member 12 having a center axis 20 in a stationary first position by any suitable device (not shown);

(b) locating from the end of the threaded member, in a first plunge cut, moving an end mill cutting tool (having a selected radius size with respect to the center axis 20 of the threaded member 12 so that the offset distance between the center of the end mill 28 and the center axis 20 is approximately equal to the radius 32 of the end mill 28, thus forming a first concave curved facet 26 in the cutting tip 10;

(c) turning the threaded member 12 through a first angle α with respect to the stationary first position (described above), fixing the threaded member, and then making a second plunge cut as in step (b) above;

(d) turning the threaded member 12 through a second angle α with respect to the stationary first position and fixing the threaded member 12 and then making a third plunge cut.

In a preferred embodiment of the method of the invention, the angle α is 120° and three curved facets 26 are produced on the cutting tip 10.

If the angle α is 90°, and a fourth plunge cut is made as described above, four curved facets 25 result on the cutting tip; and if the angle α is 75° and five plunge cuts are made, five curved facets result on the cutting tip.

Figure 3:
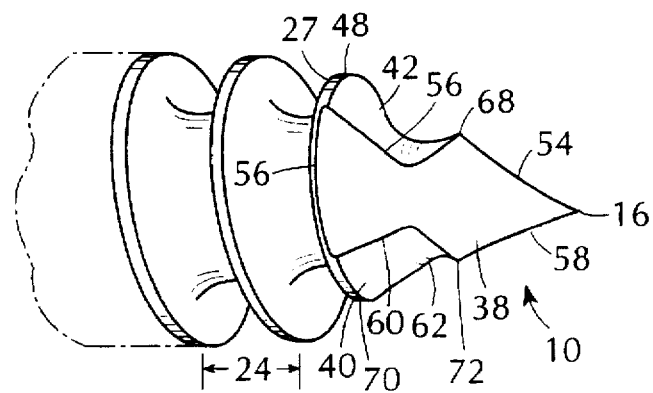
FIG. 3 is an enlarged lateral plan view of the cutting tip of FIGS. 1 and 2 showing a 3-faceted cutting tip in one embodiment of the invention which was formed by the method of the invention, with the cutting tip rotated as it would be inserted clockwise through an angle of about 240° as compared with the view of FIGS. 1 and 2.

In FIG. 3, the cutting tip shown in FIGS. 1 and 2 is rotated as it would be inserted into bone or skin clockwise through an angle of about 240°. Second facet 38 now can be seen. Portion 40 of the thread used to form the tip (not shown) remains in existence after formation of the cutting tip 10. Portion 42 is the beginning portion of the first full, complete, and uninterrupted thread 27. Portions 40 and 42 are not facets. Other corresponding parts of cutting tip 10 are shown and labelled correspondingly in FIG. 3.

Figure 4:
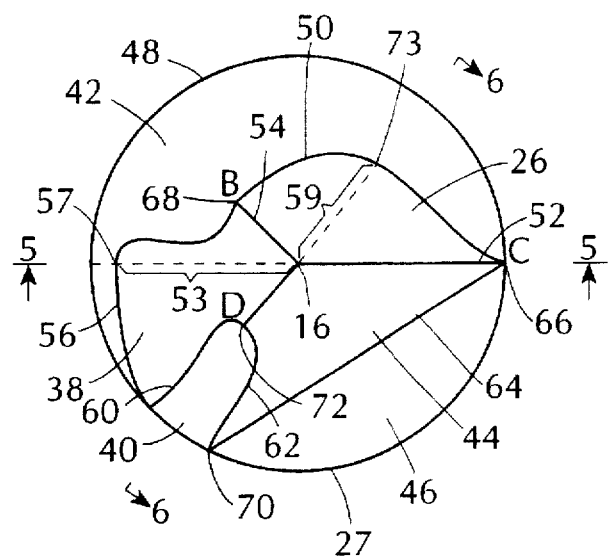
FIG. 4 is an end view of the cutting tip of FIG. 3 viewed head-on towards the tip end, showing three facets and a remaining portion of thread which was part of the original thread of the threaded member before the tip was manufactured, the original thread having been used to form the cutting tip therefrom.

In FIG. 4, the cutting tip 10 of FIG. 3 is shown in a head-on view; and the three concave curved facets 26, 38, and 44 are shown. Also shown is portion 40 of the cut thread which was cut by cutter 28 and was used to form cutting tip 10. Only portion 40 of the cut thread remains in existence. Additionally, portions 42 and 46 of the adjacent thread (which is first full thread 27, also shown in FIG. 2) are depicted in FIG. 4. Portion 46 is a chip clearance portion. The outer circumference 48 of first full thread 27 is shown and labelled. Tip end 16 can also be seen in FIG. 4. First facet 26 has a substantially triangular shape formed by three curved lines which include curved line 50, ridge 52, and ridge 54. Second facet 38 is not substantially triangular but rather has a shape as shown which is somewhat irregular and which is bounded by curved line 56, ridge 54, ridge 58, and curved line 60. Third facet 44 has a shape as shown which is substantially triangular and is bounded by ridge 58, ridge 52, curved line 62, and line 64. Point 66, point 68, and tip end 16 are the point extremities of first facet 26. Point 66, point 70, and tip end 16 form the point extremities of third facet 44. Point 68, point 72, and tip end 16 are the point extremities of the second facet 38. It is noted that portions 42 and 46 of first full thread 27 are connected and continuous (i.e., first full thread 27 is not interrupted anywhere along its entire circumference). Also, point D is not a cutting point. The points B (68), C (66) and 70 are cutting points.

Figure 5:
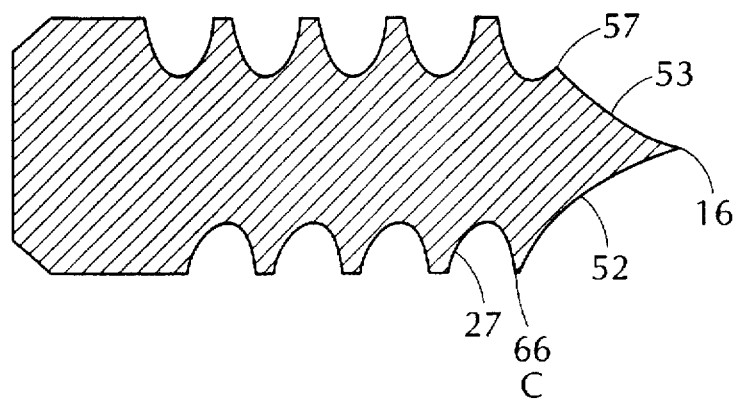
FIG. 5 is a cross-sectional view taken along the line 5—5 in FIG. 4.

In FIG. 5, a cross-sectional view taken along the line 5—5 in FIG. 4 shows tip end 16. First full thread 27, is shown, as well as portion 40 of the cut thread (from which the three facets 26, 38, 44 were formed). FIG. 5 is a cross-sectional view of the suture anchor 14 shown in FIG. 2, but rotated with respect to the view of FIG. 2. Ridge 52 and line segment 53 shown in a dotted line in FIG. 4, together with point C (i.e., 66) and point 57 on curved line segment 56, are shown in FIG. 5.

Figure 6:
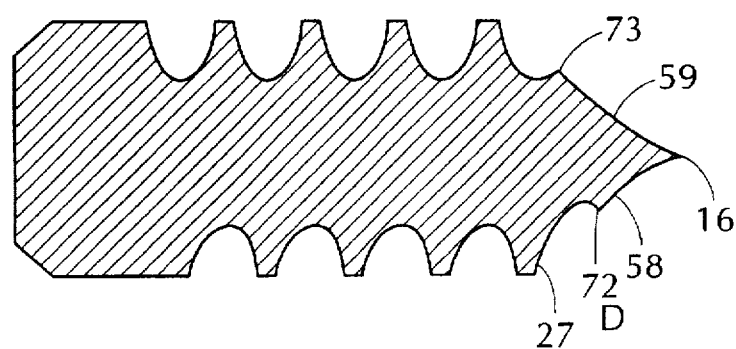
FIG. 6 is a cross-sectional view taken along the line 6—6 in FIG. 4.

FIG. 6 is a cross-sectional view taken along the line 6—6 in FIG. 4 of the threaded member 12 shown in FIGS. 2 and 5, but rotated with respect to the view of FIG. 5. Ridge 58 and line segment 59 shown in FIG. 4, together with point D (i.e., 72) and point 73 on curved line 50, are shown.

Figure 7:
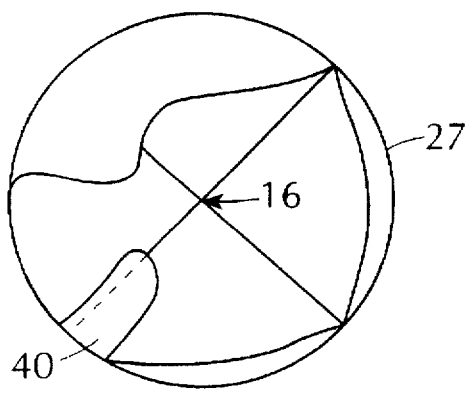
FIG. 7 is a draftsman's rendition of an end view of an embodiment of a cutting tip of the invention having four facets, as viewed head-on at the tip end.

In FIG. 7, a four-faceted cutting tip is depicted, with tip end 16 and first full thread 27 shown, together with remaining portion 40 which remains of the cut thread after the tip 10 has been cut therefrom.

Figure 8:
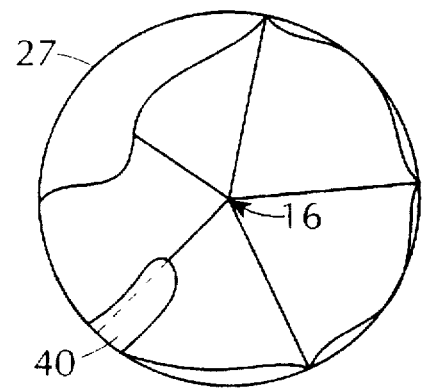
FIG. 8 is a draftsman's rendition of an end view of an embodiment of a cutting tip of the invention having five facets, as viewed head-on at the tip end.

In FIG. 8, a five-faceted cutting tip is shown, with tip end 16, first full thread 27, and remaining portion 40 of the cut thread after the tip 10 has been cut therefrom.

Figure 9:
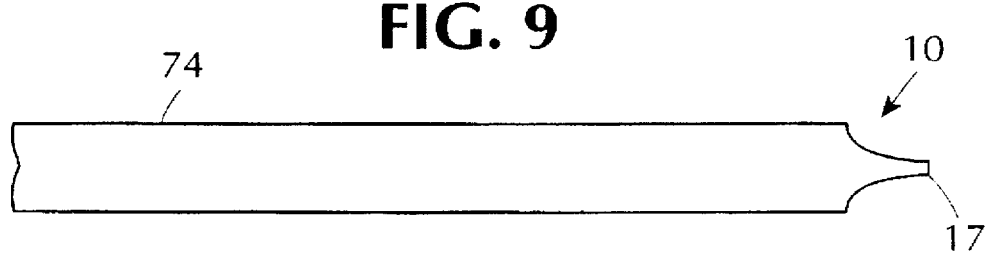
FIG. 9 is a lateral plan view of an embodiment of the cutting tip of the invention positioned on an unthreaded pin, with the end of the cutting tip having been cut off blunt.

In FIG. 9, pin 74 having no threads is shown with the cutting tip 10 of the invention and with tip end 16 modified so that it is a blunt tip end 17 which was formed by removing with the cutter a very small amount of the point from tip 16 (for example 0.005 inches).

FIG. 10 is a figure taken from U.S. Pat. No. 4,978,350, in which an embodiment of an Apex® pin 74 having three flutes 76 and a plurality of interrupted threads 78 is shown. This figure is being provided so as to illustrate an example of a flute (which is not present in the cutting tip of the present invention).

FIGS. 11-15 are 5 photographs (with magnifications printed thereon) taken by use of an electron microscope of five views of an embodiment of a cutting tip according to the invention. These are photographs of a cutting tip which was not the same tip that was used by the draftsman to produce FIGS. 1-6. There are some very slight differences in the two cutting tips depending upon how the tips were positioned during the cutting of the tip; however, the main features of the cutting tips are the same and demonstrate the reproducibility of the cutting tip of the invention and its method of manufacture.

Figure 11:
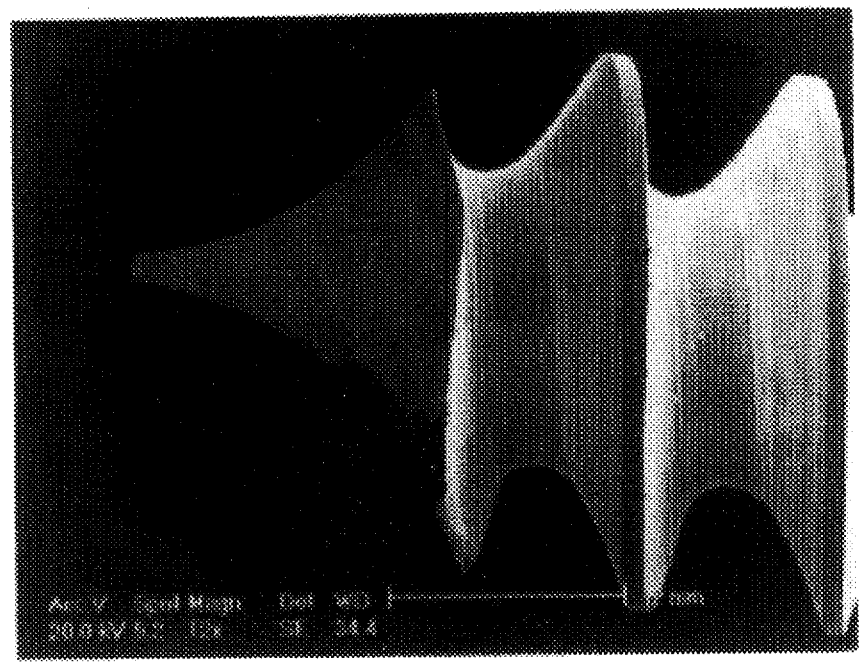
FIGS. 11–15 are photographs with magnifications indicated of a preferred embodiment of a cutting tip of the invention, which was made having three facets.

FIG. 11 (photograph 1) corresponds substantially to FIGS. 1 and 2 but with the tip end pointing to the left rather than to the right.

Figure 12:
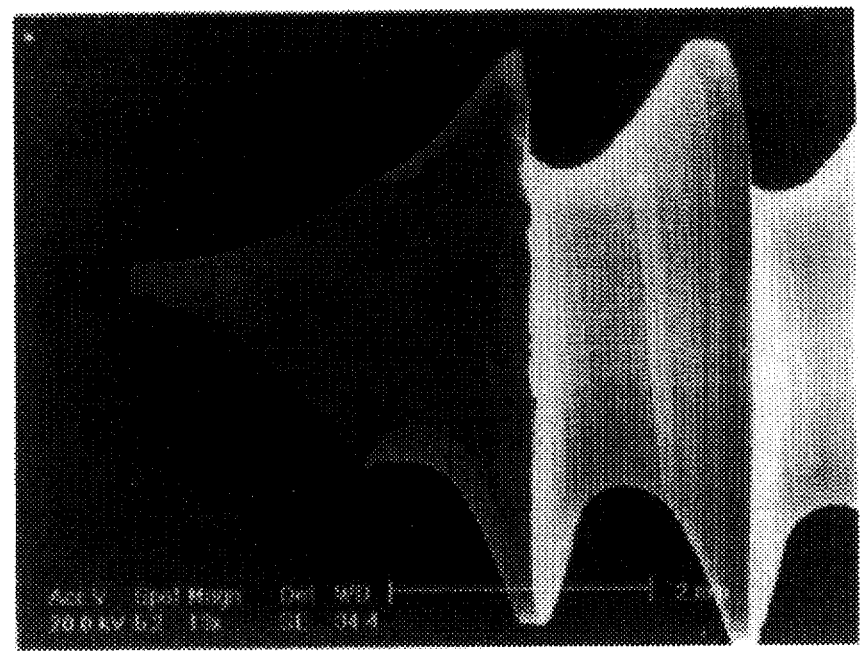

FIG. 12 (photograph 2) corresponds substantially to FIG. 3 but viewed with the tip end pointing to the left rather than to the right.

Figure 13:
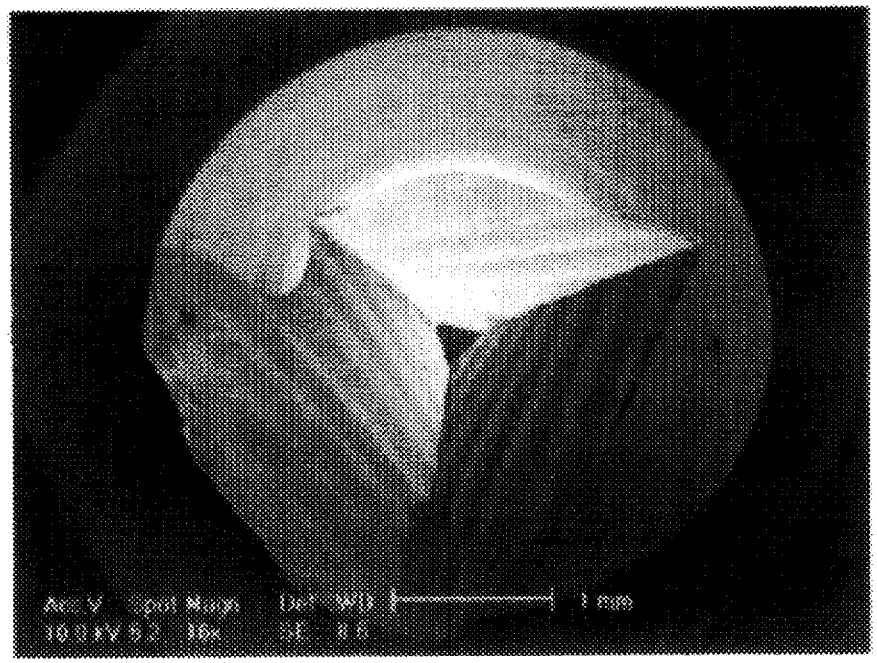

FIG. 13 (photograph 3) corresponds substantially to FIG. 4.

Figure 14:
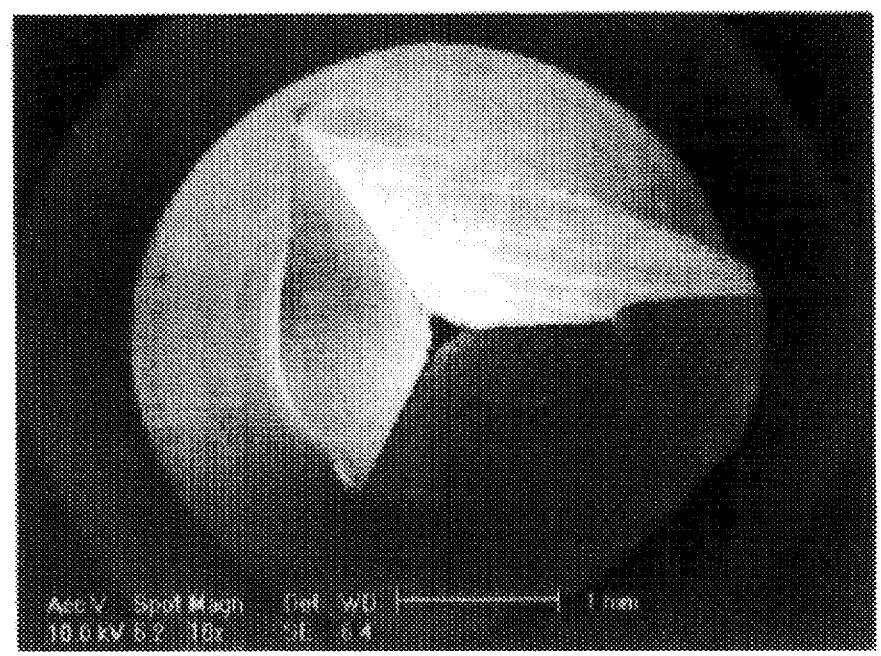

FIG. 14 (photograph 4) is a view of the cutting tip rotated counterclockwise 90° with respect to the view of FIG. 4.

Figure 15:
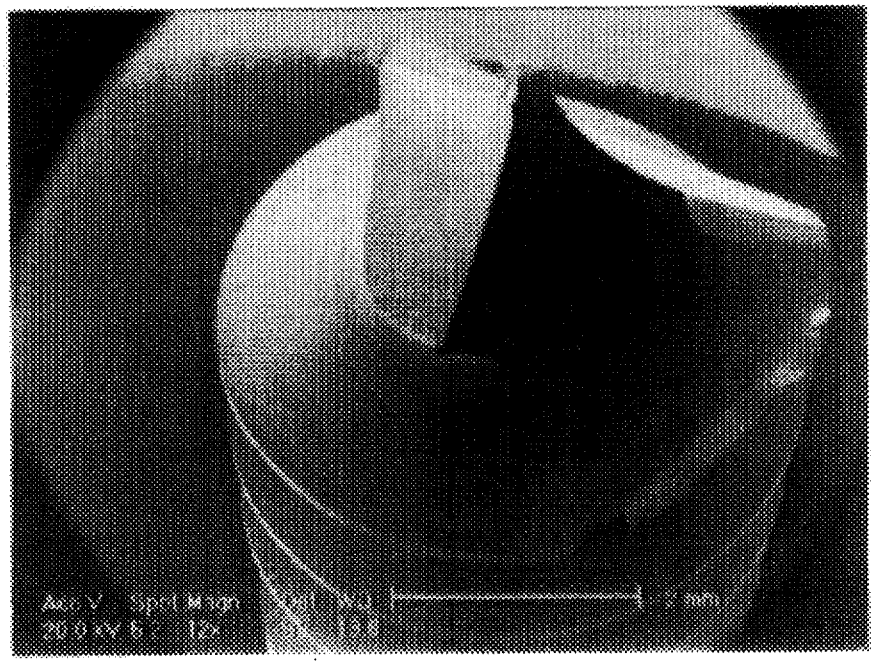

FIG. 15 (photograph 5) is a view which was not shown in the drawings and which clearly shows the beginning of the first full, complete, and uninterrupted thread located adjacent to the cutting tip. Photograph 2 also shows this beginning of the first full thread (as well as the portion 40 of cut thread used to form the tip, portion 40 being located at the top of the photograph). The differences in depths in the tip and threaded member are clearly visible in the photographs and especially in photograph 5.

The cutting tip of the invention is characterized by the following features. It has facets which are concave in shape, as opposed to having flat surfaces or convex surfaces. It has no flutes (which are similar to troughs and which would interrupt one or more threads). It can be positioned either on a threaded member or on an unthreaded pin. It is self locating.

The cutting tip of the invention can be viewed as being a modified trocar point (which is different from prior art trocars in that the cutting tips of the invention have concave curved surfaces, whereas prior art trocars have flat surfaces).

The new cutting tip design results in a sharp point that does not skid off a surface and pierces that surface with relative ease. This shape also removes less thread from the threaded member than in any other known cutting tip shape of the prior art, and it is a very simple shape and is very easily produced.

The cutting tip of the invention is characterized by having built-in chip clearance.

The cutting tip of the invention is characterized by having a minimum of thread loss after formation of the cutting tip and a maximum number of full threads, and this is especially important on suture anchors for good holding strength.

The tip penetrates the bone or skin without skidding or sliding off the bone or skin surface. The initial contact of the cutting tip with the bone or skin surface is all in a forward motion, and the cutting tip is able to penetrate the surface where there previously was no hole in the surface (i.e., the cutting tip is self-penetrating).

When the cutting tip of the invention is present on a suture anchor, as much thread as possible is retained on the threaded member after the cutting tip has been produced. This preserves the holding strength of the thread.

The Apex® pin, unlike the cutting tip of the present invention, has flutes for relief. See FIG. 10.

In the manufacture of the preferred cutting tip of the invention having three facets, there is one set-up, and the threaded member is rotated three times and three cuts are made. The cutting tip is thus very simply completed. Likewise, for four facets, the threaded member is rotated four times and four cuts are made; and for five facets, five rotations and five cuts are made. As seen in FIGS. 2 and 4, a ridge 52, 54 remains on the threaded member 12 between any two plunge cuts made in the preparation of the cutting tip, and these ridges intersect the thread at increasing distances from the centerline 20. The feature of the triangle shaped pyramid formed when the three facets 26, 38 and 44 are cut is a characteristic feature of the three faceted cutting tip 10 of the invention. As shown in FIGS. 1 and 4, as one looks at the cutting tip 10 head on, the end points of where the facets meet are progressively farther from the center point. Thus, point C 66 is farther from the centerline than point B 68. And as a result of point B 68 being closer to the centerline 20, point B 68 will make contact and cut a small portion of thread as one-third of a turn is made. Then point C 66 will cut an additional portion of bone. And as one continues on, point D will cut some more. That is, as the cutting tip is cutting through a surface plane, the contact with the plane (which is the cutting surface) moves so that the ridge line intersects the thread at increasing diameters so as to provide various cutting edges until a full thread circumference is completed. This provides a self-tapping feature which is achieved in a different way from what has been done before in the prior art.

Stated in another way, the cutting tip 10 is defined in terms of a plane, with the tip end 16 first intersecting that plane, then point B 68, then point C 66, and then point D 72. The ridge that is left between plunge cuts made to form the cutting tip 10 intersects the thread which was (were) used to form the facets at increasing diameters (i.e., perpendicular distances from the centerline 20).

The facets of the cutting tip are concave. Then, the non-fluted design of the cutting tip of the invention has the ability to carry debris and prevent jamming or clogging. The thread cuts and then occupies the space that it has cut so that there is a minimal amount of debris. Less burr is created than in the prior art devices, and no deburring operation is required in the manufacture of the cutting tip of the invention.

I claim:

1. An apparatus comprising a self-penetrating and self-locating fluteless cutting tip positioned on a substantially cylindrical-shaped threaded member having an axis, said apparatus comprising:

a multi-faceted tip located adjacent to a plurality of threads including an uninterrupted thread immediately adjacent to said tip and a distance between two adjacent threads equal to pitch p and a number of curved facets which is at least 3, said facets being provided around a single intercepted thread circumference, thereby resulting in a built-in chip clearance for chips generated during cutting and resulting in a full, complete and uninterrupted thread immediately adjacent to said tip.

2. An apparatus according to claim 1, wherein said cutting tip has three concave curved facets.

3. An apparatus according to claim 2, wherein said cutting tip has four concave curved facets.

4. An apparatus according to claim 2, and including also said threaded member on which said cutting tip is positioned.

5. An apparatus according to claim 4, wherein said threaded member is a screw.

6. An apparatus according to claim 4, wherein said threaded member is a threaded pin.

7. An apparatus according to claim 4, wherein said threaded member is a suture anchor.

8. An apparatus according to claim 4, wherein said threaded member is a tap.

9. An apparatus according to claim 4, wherein said threaded member is a drill.

10. An apparatus according to claim 4, wherein said threaded member is a reamer.

11. A cutting tip formed by a method of making a novel fluteless cutting tip which is self-penetrating and self-locating and located on a threaded member having a center axis and threadings and a threaded member diameter, said method comprising:

(a) holding said threaded member in a stationary first position;

(b) in a first plunge cut moving a cutter having a cutter center axis and a cutter diameter having a diameter first end and a diameter second end with respect to said center axis of said threaded member, so that said diameter first end is substantially tangent to said center axis of said threaded member and so that said cutter center axis is substantially perpendicular to said center axis of said threaded member, thus forming a first curved facet in said cutting tip;

(c) turning said threaded member through a first angle α with respect to said stationary first position, fixing said threaded member in a second stationary position, and then making a second plunge cut as in step b (above), thus forming a second curved facet in said cutting tip;

(d) turning said threaded member further through a second angle α with respect to said stationary first position and fixing said threaded member in a third stationary position and then making a third plunge cut (as in step b above), thus forming a third curved facet in said cutting tip.

12. A cutting tip according to claim 11, wherein said angle α is 120° and wherein three curved facets are produced in said cutting tip.

13. An apparatus comprising a self-penetrating and self-locating fluteless cutting tip positioned on a substantially cylindrical-shaped threaded member having an axis, said apparatus comprising:

a multi-faceted tip located adjacent to a plurality of threads including an uninterrupted thread immediately adjacent to said tip such that said uninterrupted thread runs continuously into said tip without any unthreaded shaft or partially threaded shaft located between said tip and said uninterrupted thread, and having a distance between two adjacent threads equal to pitch p and having a number of curved facets which is at least three, said facets all intersecting a single intercepted thread circumference, thereby resulting in a built-in chip clearance for chips generated during cutting and resulting in a full, complete, and uninterrupted thread immediately adjacent to said tip, wherein any two adjacent facets of said at least three facets intersect each other so as to form a ridge and wherein each ridge intersects said single intercepted thread circumference at an intersection so as to form a cutting point at each such intersection of a ridge and said single intercepted thread circumference.

14. An apparatus according to claim 13, wherein said cutting tip has three concave curved facets, three ridges, and three cutting points.

15. An apparatus according to claim 14, wherein said cutting tip has four concave curved facets, four ridges, and four cutting points.

* * * * *